(12) United States Patent
Bailey

(10) Patent No.: US 10,405,991 B2
(45) Date of Patent: Sep. 10, 2019

(54) INSTRUMENT FOR POSITIONING A CUP COMPONENT OF AN ORTHOPAEDIC JOINT PROSTHESIS

(71) Applicant: Andrew Bailey, Leeds (GB)

(72) Inventor: Andrew Bailey, Leeds (GB)

(73) Assignee: DEPUY IRELAND UNLIMITED COMPANY (IE)

( * ) Notice: Subject to any disclaimer, the term of this patent is extended or adjusted under 35 U.S.C. 154(b) by 516 days.

(21) Appl. No.: 15/024,420

(22) PCT Filed: Sep. 29, 2014

(86) PCT No.: PCT/GB2014/052933
§ 371 (c)(1),
(2) Date: Mar. 24, 2016

(87) PCT Pub. No.: WO2015/044685
PCT Pub. Date: Apr. 21, 2005

(65) Prior Publication Data
US 2016/0235551 A1    Aug. 18, 2016

(30) Foreign Application Priority Data
Sep. 30, 2013 (GB) .................................. 1317287.9

(51) Int. Cl.
*A61B 17/58* (2006.01)
*A61B 17/60* (2006.01)
(Continued)

(52) U.S. Cl.
CPC .. *A61F 2/4609* (2013.01); *A61F 2002/30484* (2013.01); *A61F 2002/30522* (2013.01);
(Continued)

(58) Field of Classification Search
CPC combination set(s) only.
See application file for complete search history.

(56) References Cited

U.S. PATENT DOCUMENTS

| 5,108,448 A | 4/1992 | Gautier |
| 5,171,243 A | 12/1992 | Kashuba |

(Continued)

FOREIGN PATENT DOCUMENTS

| CN | 103167838 A | 6/2013 |
| DE | 19704577 A1 | 8/1998 |

(Continued)

*Primary Examiner* — Sameh R Boles

(57) ABSTRACT

An instrument (200) for positioning a hollow cup component (202) of an orthopedic joint prosthesis and assembly thereof are described. The instrument includes a support member (204) having a plurality of jaw members (208) unitarily formed around its periphery. Each of the jaw members has a cup engaging limb (210) extending in a first direction to be received in a recess on an external side wall of the cup component. Each jaw member is pivotable between an engaged position in which the cup engaging limbs are displaced inwardly and a disengaged position in which the cup engaging limbs are displaced outwardly allowing the cup component to be removed from between the jaw members. An actuator (216) is operable to adopt an engaged configuration in which the actuator acts on all the jaw members to urge them into the engaged position or a disengaged configuration in which the actuator does not act on any of the jaw members to urge them into the engaged position and all the jaw members can adopt the disengaged position.

15 Claims, 3 Drawing Sheets

(51) Int. Cl.
 *A61F 2/00* (2006.01)
 *A61F 2/46* (2006.01)
 *A61F 2/30* (2006.01)

(52) U.S. Cl.
 CPC ............... *A61F 2002/30579* (2013.01); *A61F 2002/4622* (2013.01); *A61F 2002/4624* (2013.01); *A61F 2002/4627* (2013.01); *A61F 2002/4628* (2013.01)

(56) References Cited

U.S. PATENT DOCUMENTS

| | | | |
|---|---|---|---|
| 5,417,696 A | 5/1995 | Kashuba | |
| 5,507,748 A | 4/1996 | Sheehan | |
| 5,683,399 A | 11/1997 | Jones | |
| 5,928,287 A | 7/1999 | Keller | |
| 6,022,357 A | 2/2000 | Reu | |
| 6,045,583 A | 4/2000 | Gross | |
| 6,352,559 B1 | 3/2002 | Church | |
| 6,468,281 B1 | 10/2002 | Badorf | |
| 7,931,656 B2 | 4/2011 | Parry | |
| 8,277,457 B1 | 10/2012 | Burgi | |
| 8,535,324 B2 | 9/2013 | Aux Epaules | |
| 2004/0215200 A1* | 10/2004 | Tornier | A61F 2/4609 606/91 |
| 2005/0137603 A1 | 6/2005 | Belew | |
| 2005/0149047 A1 | 7/2005 | Parry | |
| 2005/0209597 A1 | 9/2005 | Long | |
| 2005/0228394 A1 | 10/2005 | Bihary | |
| 2006/0149285 A1 | 7/2006 | Burgi | |
| 2006/0167462 A1 | 7/2006 | Raugel | |
| 2006/0229630 A1 | 10/2006 | Collins | |
| 2009/0234453 A1 | 9/2009 | Steinberg | |
| 2009/0248027 A1 | 10/2009 | Imhof | |
| 2009/0281550 A1 | 11/2009 | Keller | |
| 2011/0288649 A1 | 11/2011 | Ratzel | |
| 2012/0029524 A1 | 2/2012 | Imhof-Röthlin | |
| 2012/0059383 A1 | 3/2012 | Murphy | |
| 2013/0079785 A1 | 3/2013 | Burgi | |

FOREIGN PATENT DOCUMENTS

| | | |
|---|---|---|
| DE | 19722923 A1 | 8/1998 |
| DE | 10128234 A1 | 1/2003 |
| DE | 10250390 A1 | 5/2004 |
| DE | 102008049661 A1 | 4/2010 |
| EP | 0811360 A2 | 12/1997 |
| EP | 2347736 A1 | 7/2011 |
| FR | 2797180 A1 | 2/2001 |
| FR | 2809305 A1 | 11/2001 |
| FR | 2877210 A1 | 5/2006 |
| FR | 2917288 A1 | 12/2008 |
| GB | 2299758 A | 10/1996 |
| GB | 2473610 A | 3/2011 |
| WO | WO 2008099242 A1 | 8/2008 |

\* cited by examiner

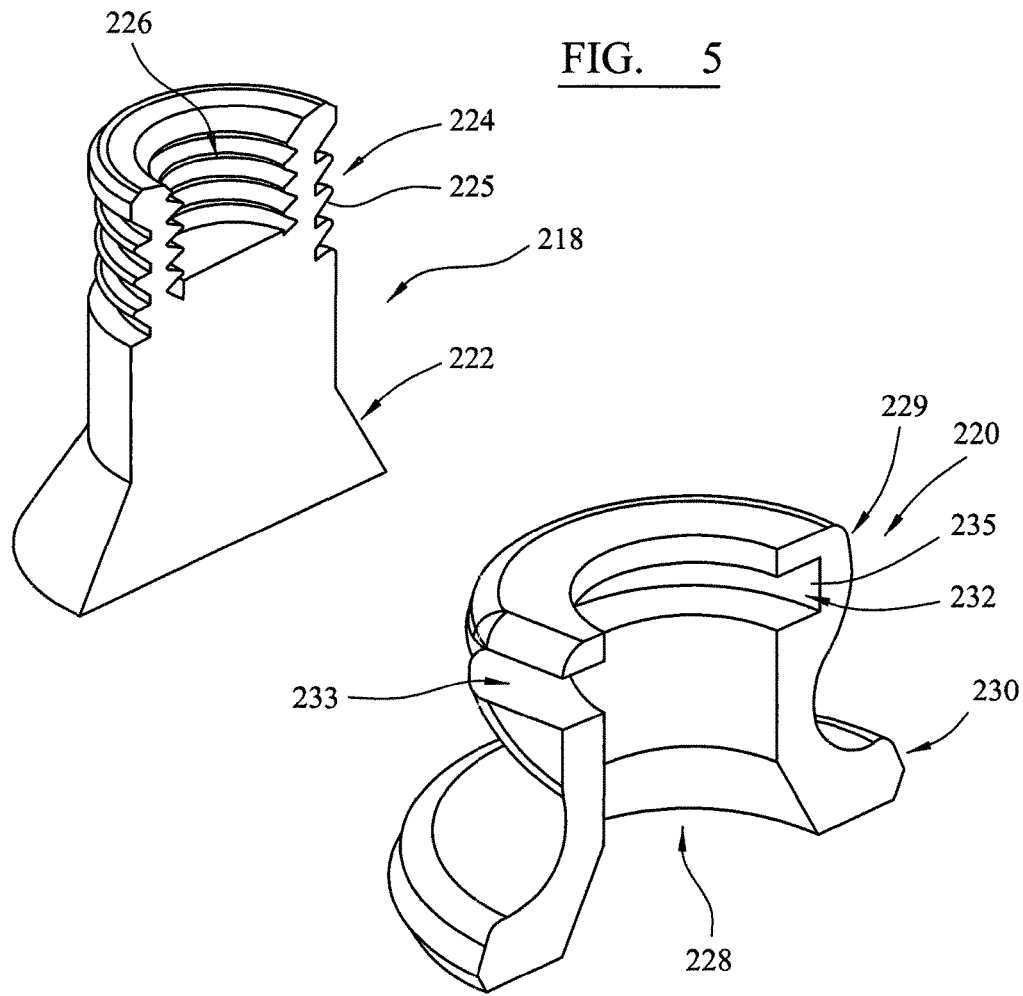
FIG. 5
FIG. 6
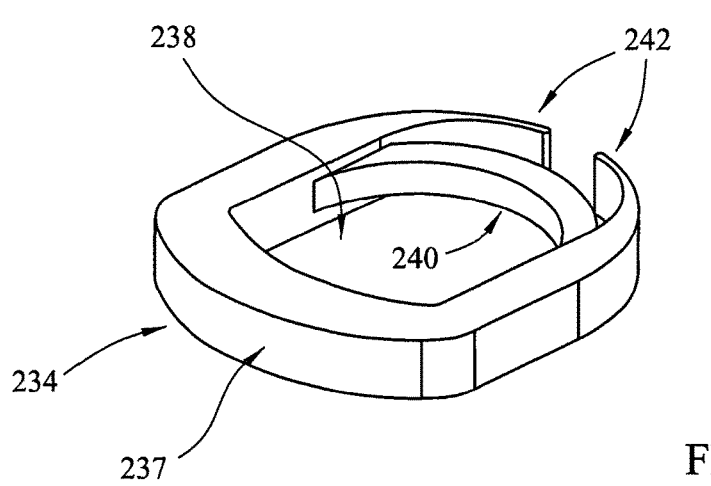
FIG. 7

INSTRUMENT FOR POSITIONING A CUP COMPONENT OF AN ORTHOPAEDIC JOINT PROSTHESIS

CROSS REFERENCE TO RELATED PCT APPLICATION

This application is a National Stage 35 U.S.C. 371 of International Patent Application No. PCT/GB2014/052933 filed Sep. 29, 2014, which claims priority to United Kingdom Application No. GB1317287.9, filed Sep. 30, 2013, both of which are incorporated by reference in their entireties.

This invention relates to an instrument for positioning a cup component of an orthopaedic joint prosthesis.

Certain orthopaedic joint prostheses include a hollow cup with an inner surface which defines a generally hemispherical hollow region, and another component which has a spherical part which can be received in the hollow region for articulation relative to the cup component. Such joint prostheses can include hip joint prostheses and shoulder joint prostheses. The exterior of the cup will contact the prepared surface of the patient's bone in which the component is to be implanted. The interior of the cup will present a smooth bearing surface to the spherical convex part of the other component of the joint prosthesis. The bearing surface can be provided by a single piece cup component. Alternatively, the cup component can comprise a shell part which contacts the prepared surface of the patient's bone, and a bearing part which provides the bearing surface, and which fits into the shell part. The bearing part can be made from a material which is different from the material of the shell part: for example the bearing part can be made from a polymeric material (such as polyethylene) or a ceramic material and the shell part (and the spherical convex part of the other component) can be made from a metal (such as a cobalt-chromium based alloy, or a stainless steel, or a titanium based alloy).

It is important that the components of an orthopaedic joint prosthesis are positioned accurately in a patient's bone. Both location and alignment are important. Accurate positioning of a component requires that the component be engaged by an appropriate instrument, allowing considerable force to be applied to the component if and as necessary (for example through use of an impactor instrument). However, it can be important not to contact the external surface or the internal surface or both of the component with the instrument, especially the internal surface when it has been provided with a smooth polished bearing surface. Scratching or otherwise damaging that surface can impair the bearing properties of the prosthesis.

U.S. Pat. No. 5,171,243 discloses an acetabular cup for use in a hip joint prosthesis. The cup comprises a shell which has a circumferential groove cut into its inner surface. The groove can received a flange at the free end of an insertion tool so that the cup is retained on the instrument, allowing the shell to be manipulated using the instrument. The grooved shell part receives a bearing part which has a smooth inner surface against which a bearing surface of another component of the joint prosthesis can articulate. The shell part can have fastening holes extending through its wall through which bone screws can extend to fasten the shell part to the surface of a bone.

WO-A-2008/099242 discloses an instrument for gripping a cup component of an orthopaedic joint prosthesis. The instrument has a plurality of jaw members which extend radially from a central drive shaft. The jaw members can be made to slide radially inwardly so that they engage the outside wall of a cup component. Each of the jaw members has a pin at one end which is received in a spiral track on a drive plate. The jaw members are made to slide radially by rotating the drive plate.

The present invention provides an instrument for positioning a cup component of an orthopaedic joint prosthesis, which includes jaw members attached to a support member and which can pivot relative to the support member between engaged and disengaged positions.

Accordingly, the invention provides an instrument for positioning a hollow cup component of an orthopaedic joint prosthesis, which comprises a support member having a plurality of jaw members around a periphery of the support member. The jaw members can be unitarily or integrally formed with the support member around its periphery. Each of the jaw members can have a cup engaging limb which extends from the support member in a first direction to be received in a recess on an external side wall of the cup component. Each jaw member can be pivotable between an engaged position in which the cup engaging limbs are displaced inwardly and a disengaged position in which the cup engaging limbs are displaced outwardly allowing the cup component to be removed from between the jaw members. The instrument can further comprise an actuator operable to adopt an engaged configuration, in which the actuator acts on all the jaw members to urge them into the engaged position, or a disengaged configuration, in which the actuator does not act any of the jaw members to urge them into the engaged position and all the jaw members can adopt the disengaged position.

Providing the plurality of jaw members as an integral or unitary part of the support member reduces the number of parts of the instrument and simplifies its construction, its operation and makes it easier to clean. The instrument of the invention has the advantage that the number of parts from which it is made is small. Furthermore, assembly of the instrument from its parts can be simple. These advantages mean that the instrument can be manufactured simply and at low cost.

The instrument can have at least two jaw members, for example three jaw members, and preferably more than three jaw members. It will sometimes be preferred that the jaw members are spaced apart equally around the support member so that, for example, when the instrument has three jaw members, the angle between adjacent jaw members is 120°. It will generally be preferred that each of the jaw members is mounted on the support member so that it can pivot between engaged and disengaged positions, with the actuator acting on the jaw members to cause each of them to move between its engaged and disengaged positions.

The instrument can have an array of jaw members provided around at least part of its periphery. The spacing between the jaw members of the array can be less than the width of each of the jaw members. The instrument can have at least 10 jaw members in an array, or at least 20 jaw members, or at least 30 jaw members, or at least 40 jaw members. The jaw members of the array can be spaced approximately uniformly around the periphery of the instrument, preferably around the entire periphery of the instrument.

The jaw members can be provided around the entire periphery of the support or provided as a plurality of groups of jaw members around the periphery, with regions having no jaw members being provided between adjacent groups of jaw members. Each group can have one jaw member or a plurality of jaw members. At least two groups can be provided and preferably at least three groups.

If less than all of the jaw members are able to pivot relative to the support member, separation of the instrument from a cup component might require lateral movement of the instrument relative to the cup component. However, it is preferred that each of the jaw members is pivotable. This can facilitate separation of the instrument from a cup component.

The support member should be capable of engaging the cup component so that a force can be applied to the cup component through the support member in a direction into or towards the interior of the cup component. The support member can engage the rim of the cup component at the open face of the cup component.

Preferably the transverse dimension of the support member is not greater than the transverse dimension of the cup component. This means that the support member does not completely mask sight of the cup component. It also means that the support member will not impinge on bone tissue adjacent to the site at which the cup component is implanted.

The support member can be in the form of a plate which can be fitted on to the cup component. The plate can have openings extending through it allowing the user to inspect the interior of the cup component. The support member can be in the form of a plurality of limbs.

The plurality of jaw members can be formed integrally or unitarily with the support member. For example the jaw members can be formed integrally or unitarily with the support member by moulding, so that the jaw members are formed as a single body with the support member. For example, one or more of the jaw members can be formed with the support member in a moulding operation. A moulding operation can be used to form a jaw member which is able to pivot relative to the support member by forming a living hinge. A living hinge is formed by providing a web or portion of the material from which the jaw member and the support member are formed which is locally thin compared with surrounding material.

The or each pivotable jaw member can include a control limb which is connected to the cup engaging limb at or adjacent to the periphery of the support member, and extends inwardly from the edge of the support member where it is acted on by the actuator. When the or each pivotable jaw member is mounted on the support member at or towards the peripheral edge of the support member, the mounting can be at or closely adjacent to the connection between the cup engaging limb and the control limb so that the cup engaging limb extends from the mounting in the direction in which the first face of the support member is directed, and the control limb extends from the mounting across the second face of the support member (like a first class lever). In another construction, the or each pivotable jaw member can be mounted on the support member at or towards the end of the control limb which is remote from cup engaging limb (like a third class lever).

The or each pivotable jaw member can be biased towards its engaged position. The actuator can then be used to apply a force to the jaw member to move it towards its disengaged position.

The or each pivotable jaw member can be biased towards its disengaged position. The actuator can then be used to apply a force to the jaw member to move it towards its engaged position.

When the pivot for the jaw member is provided by a living hinge, the biasing force on the jaw member can be provided by the material of the living hinge. A biasing member can be provided as a separate component from the support member or the jaw member or each of them if required. A bias can be applied to the jaw member by the actuator.

The actuator can comprise a first shaft which engages the support member and a second shaft which is arranged so that it extends parallel to the first shaft and to engage the or each pivotable jaw member. The pivotable jaw member can be caused to move between its engaged and disengaged positions by relative movement between the first and second shafts.

The second shaft may have an upper part and a lower part and the lower part may engage the or each pivotable support member. The upper part and the lower part may define a recess between them. The recess may be sized, dimensioned or otherwise arranged to receive one or more thumbs or fingers of a user in use. The recess may include a first portion and a second portion on opposed sides of the first shaft. The first and second portions may be arranged to receive a pair of fingers of a user in use. The recess may extend around a portion of, or entirely around, a central longitudinal axis of the actuator.

The actuator can include a locking mechanism for locking the actuator against displacement under the biasing force. For example, the actuator can include a ratchet mechanism comprising a plurality of teeth which are engaged sequentially by a pawl when a first actuator shaft is moved relative to a second actuator shaft. The actuator can then include a release button by which the ratchet mechanism can be released, allowing the biasing component of the actuator to act on the jaw members. The release button can be provided in the upper part of the actuator. The release button can extend proud of an outermost surface of the upper part of the actuator.

The actuator can include a threaded mechanism for locking the actuator against displacement under the biasing force.

The actuator can include a handle by which it, and the cup component when mounted on the actuator, can be manipulated. The first shaft or the second shaft can provide the handle. It will often be preferred that the first shaft provides the handle. The handle can be part of the actuator. The handle can be provided as a separate component which can be connected to the actuator, for example by means of a threaded connection or by means of a bayonet connection.

The actuator can have an impaction surface through which an impaction force can be applied to cause the cup component to be seated fully in the prepared cavity in the patient's bone (for example, in the patient's acetabulum). The impaction surface can be provided on a handle for the actuator.

Component parts of the instrument can be made from polymeric materials or metallic materials or from both polymeric and metallic materials. Suitable polymeric materials include polyolefins, polyesters, engineering polymers such as polyetheretherketones, and acetals. Suitable metals include certain stainless steels, and titanium and its alloys. The use of polymeric materials for at least some of the component parts of the instrument has the advantage of lower cost and ease of manufacture, for example by moulding.

For many applications, the cup component will be rotationally symmetrical about a polar axis. It will often be preferred that the cup component has the shape of a portion of a sphere. As is known, the rim of a cup component to be fitted in a patient's acetabulum in a hip replacement procedure will frequently subtend an angle of at least 140° at the centre of the sphere, for example at least 150° or at least 160° or at least 170°. The rim of an acetabular cup component will frequently be circular, although sometimes the rim can have an extension on one side for example to reduce the risk of dislocation. When the rim of the cup component is circular, the rim can be planar around at least 50% of the periphery of the cup component. The plane defined by the rim can be perpendicular to the polar axis of the component.

The glenoid component of a shoulder prosthesis will generally be more shallow than the cup component of a hip prosthesis and its rim might not be circular.

The bone facing surface of the cup component can be adapted for contact with bone tissue. For example, it can be adapted to bond to the bone tissue as a result of direction interaction (for example bone ingrowth) of bone into the surface of the component, or it can be adapted to bond to the tissue by means of a bone cement material.

The cup component can have a plurality of discrete recesses arranged around its periphery in which parts of the jaw members can be received. When the cup component has discrete recesses arranged around its periphery, the number of recesses should not be less than the number of jaw members. Frequently, the number of recesses and the spacing between the recesses should correspond to the number of jaw members and the spacing between the jaw members.

The cup component can have a recess which is longer than the width of the fingers which are received in it, for example in the form of a groove which extends around at least part of the cup component. The groove can extend continuously around the entire periphery of the cup component.

The internal surface of the cup component can have a smooth surface allowing the surface to cooperate with the convex surface of a mating component in a bearing relationship. Alternatively, the cup component can be configured to receive a liner which has a smooth bearing surface so that the cup component can be considered as a shell.

The invention also provides an assembly for use in a surgical procedure to replace an orthopaedic joint, which comprises: an instrument according to the invention, and a hollow cup component of an orthopaedic joint prosthesis. A part of each of the jaw members of the instrument can be received in a recess in the wall of a cup member.

An embodiment of the invention is described below in detail, and by way of example only, and with reference to the accompanying drawings, in which:

FIG. 5 is a sectional isometric view of a first shaft member of an actuator of the instrument shown in FIGS. 1 and 2;

FIG. 6 is a sectional isometric view of a second shaft member of the actuator of the instrument shown in FIGS. 1 and 2; and FIG. 7 is an isometric view of a release button of the actuator of the instrument shown in FIGS. 1 and 2.

Figure 1:
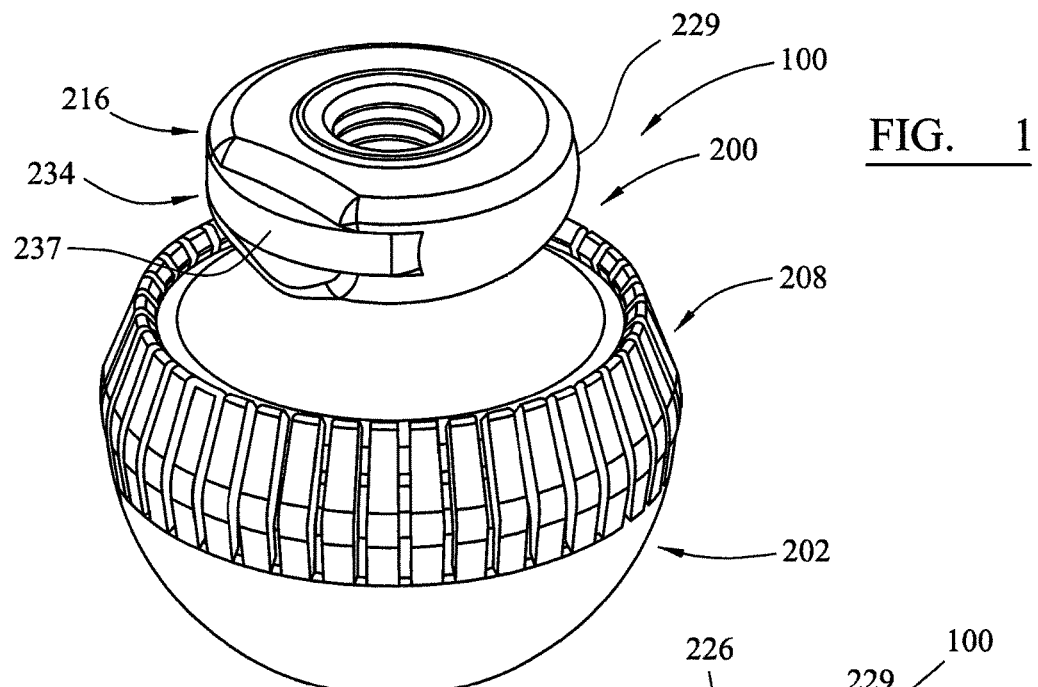
FIG. 1 is an isometric view of an assembly including an embodiment of the instrument in combination with a hollow cup component of an orthopaedic joint prosthesis.
Figure 2:
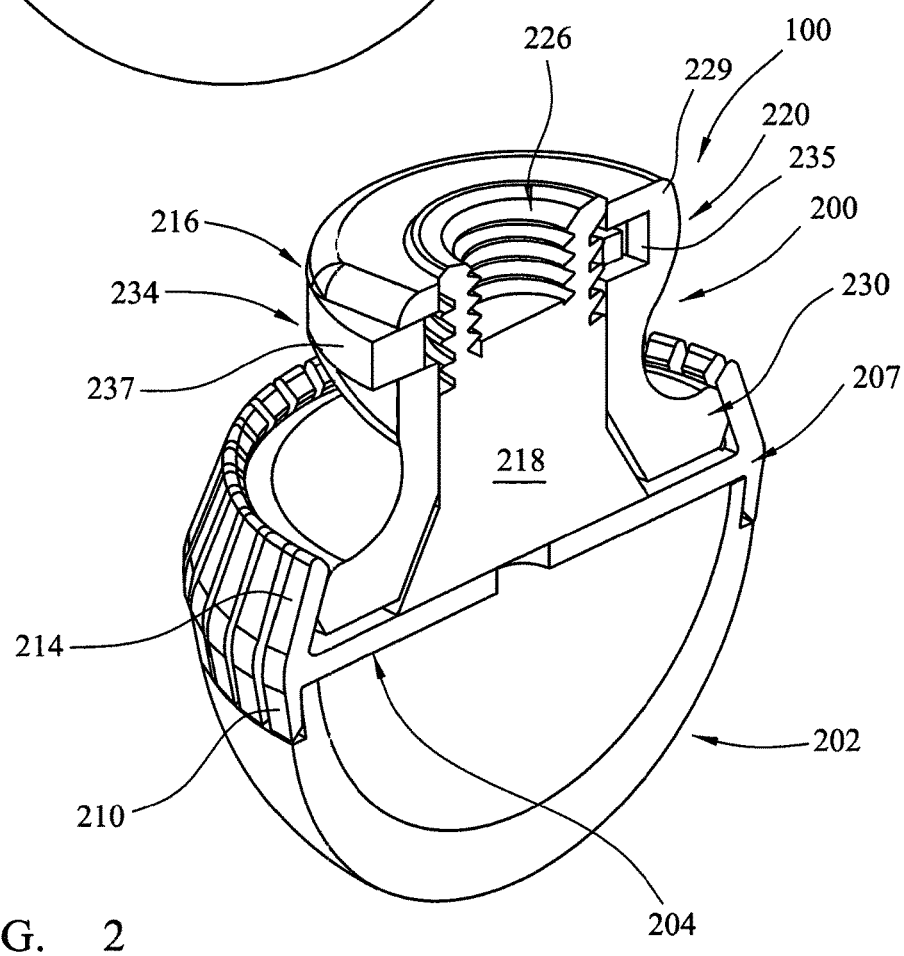
FIG. 2 is sectional isometric view of the assembly shown in FIG. 1.
Figure 3:
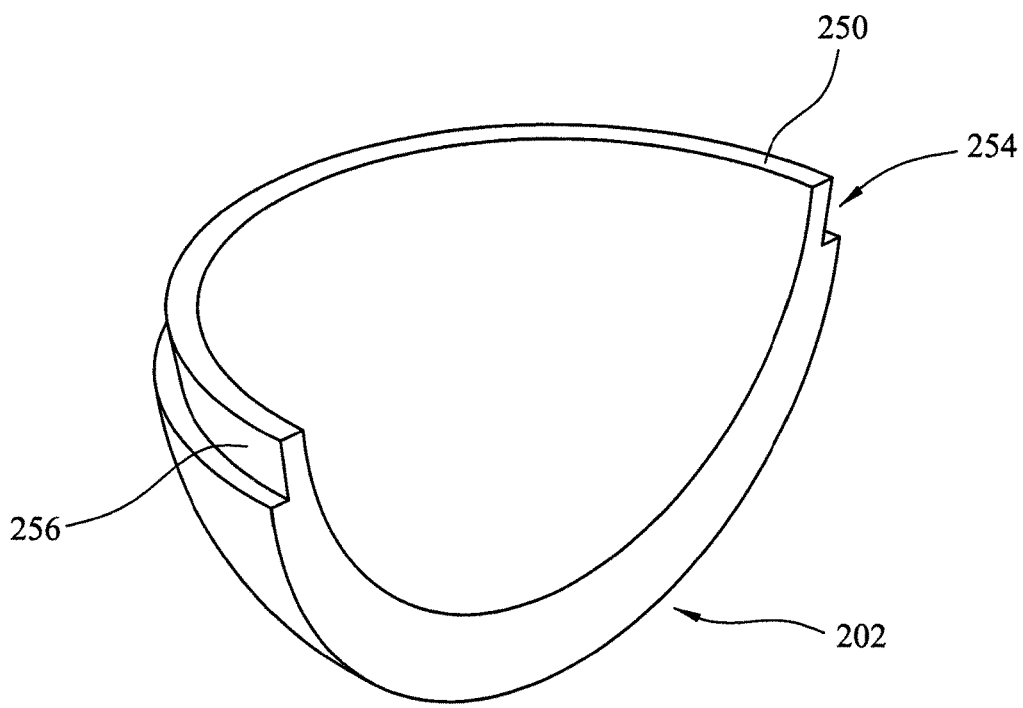
FIG. 3 is sectional isometric view of the hollow cup component of the assembly shown in FIGS. 1 and 2.

Referring to the drawings, FIGS. 1 and 2 show perspective and cross sectional perspective views respectively of an assembly 100 of an instrument 200 for positioning a hollow cup component of an orthopaedic joint prosthesis and the cup component 202. The instrument can be used for positioning an acetabular cup component of a hip joint prosthesis in a prepared cavity of a patient's acetabulum.

FIGS. 3 to 7 show perspective and cross sectional perspective views respectively of various parts of the instrument 200 and cup component 202.

Figure 4:
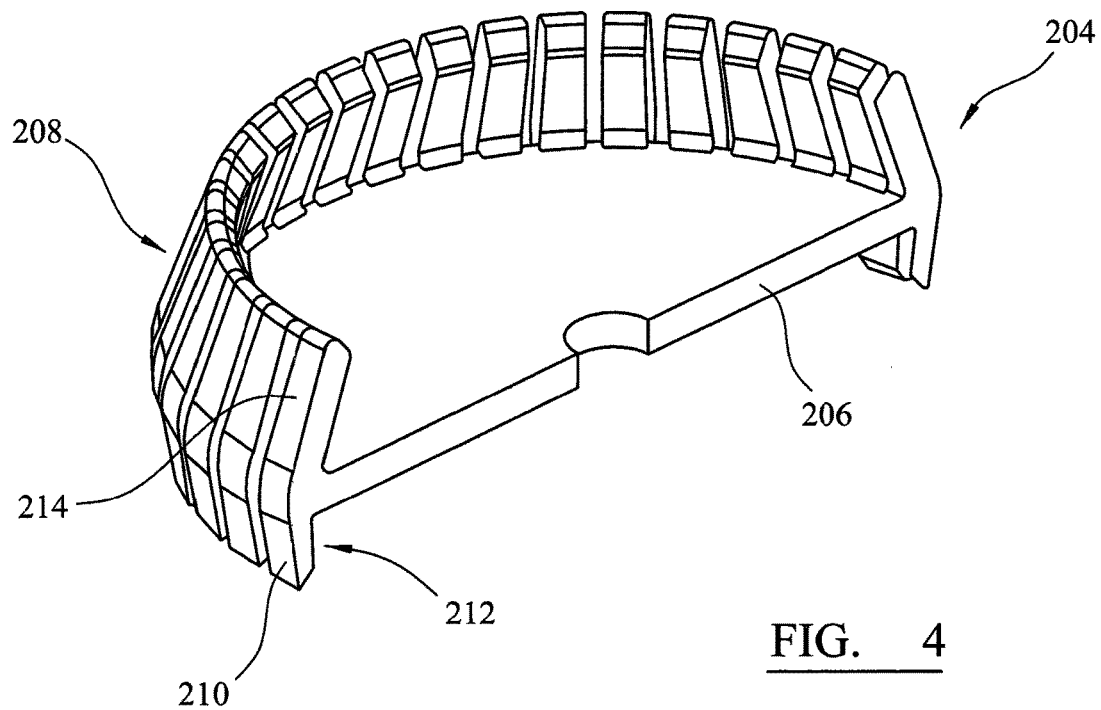
FIG. 4 is sectional isometric view of the support part of the instrument shown in FIGS. 1 and 2.

The instrument 200 includes a support member 204, a cross sectional perspective view of which is shown in FIG. 4, in the form of a circular plate 206 with a plurality of jaw members 208 at its edge and extending around the entire periphery of the circular plate 206. The support member 204 and plurality of jaw members 208 have a unitary construction and the jaw members are provided as integral parts of the support member, rather than being separate parts which are attached by a pivot mechanism. Each of the jaw members has a cup engaging limb 210 extending from the plate towards the cup component, with an inwardly directed finger 212 at its end. Each of the jaw members has a control limb 214 extending from the plate away from the cup component. The control limbs are inclined inwardly. The region 207 at which the jaw members meet the circular plate provides a live or living hinge or spring. The live hinge may also be a sprung or resilient hinge and may bias the jaw members in a preferred direction. The live spring 207 may be produce by geometric and/or materials properties of the support member 204, for example by machining away material, or molding, to produce a part thinner than the remainder of the disc 206 of the support member. In other embodiments, the live spring could be implemented by incorporating ribs or by including steel elements, for example, by overmolding the material of the support member onto a steel element or elements arranged to help to provide the resilience of the live spring.

An actuator 216 includes a first shaft 218, a cross sectional perspective view of which is show in FIG. 5, which is flared outwardly towards its distal end 222. The first shaft has a plurality of annular teeth 224 formed in an outer surface and toward its proximal end. The face of each tooth which is directed distally, e.g. face 225, is inclined to a longitudinal axis of the actuator. The first shaft 218 has a threaded bore 226 formed centrally in it at its proximal end which can receive a threaded stub on a handle (not shown). The handle can be used to manipulate the assembly 100 of the actuator and a cup component engaged with it. The handle can have an impaction surface.

The actuator 216 includes a second shaft 220, a cross sectional perspective view of which is show in FIG. 6, which has a bore 228 extending centrally through it in which the first shaft is received and can slide. The second shaft has a peripheral flange 230 at its distal end which fits under the control limbs 214 on the jaw members 208, between the control limbs and the plate 206.

The second shaft has a collar 229 at its proximal end which has a slot 232 formed in it, and extending perpendicular to the longitudinal axis of the actuator. The slot 232 is open over a portion 233 on one side. A release button 234 is fitted in the slot. The release button 234, a perspective view of which is show in FIG. 7, has a generally ring form and comprises a plate 236 which has an opening 238 extending through it. A tooth 240 is provided on the release button. The button 234 has a pair of flexible and resilient fingers 242 which can act against a wall at a blind end 235 of the slot 232 in the collar 216, to bias the button outwardly of the slot. The collar 229 has a portion cut away to expose a portion 237 of the bottom diametrically opposite the pair of fingers 242 and by which the release button can be operated by a user.

The instrument 200 is prepared for use by positioning the circular plate 206 so that is sits on the rim 250 of a cup component 202 of an orthopaedic joint prosthesis. The cup component has an annular recess 254 on its external surface which defines a lip 256 at the rim 250. The cup engaging limbs 210 of the jaw members 208 are positioned radially outward of the annular recess in the external surface of the cup component, with the inwardly directed fingers 212 below the lip 256. In some embodiments, the jaw members can be biased by the live spring toward a disengaged position so that the fingers 212 of the jaw members 208 do not engage the lip 256 so that the instrument can be easily presented to and placed on the rim 250 of the cup 202.

The first shaft 218 is displaced relative to the second shaft 220 in a direction towards the circular plate 206. This can be accomplished by the user by positioning his (or her) first and second fingers on opposite sides of the collar 229 of the second shaft, between the peripheral flange 230 and the collar 229, and positioning his thumb on the proximal end of the first shaft. The first shaft is then displaced by pushing down with the thumb while pulling up with the first and second fingers.

The displacement of the first shaft 218 relative to the second shaft has the result of the peripheral flange 230 applying an upward force on the control limbs 214, as the support plate 206 provides a reactive force to the force imparted by the flared distal part of the first shaft. The upward force applied to the control limbs 214 causes the jaw members 208 to pivot about the live hinge at the point at which they are connected to the circular plate 206, so that the cup engaging limbs 210 are displaced inwardly and the inwardly directed fingers 212 on the cup engaging limbs fit under the lip 256 on the rim of the cup component.

Movement of the proximal end of the first shaft 218 through the bore 228 in the second shaft 220 causes the release button 234 to slide in the slot 232 in the collar 216, against the biasing force provided by the flexible fingers 242 pressing against the closed end of the slot, as the annular teeth 224 on the first shaft move axially past the tooth 240 on the release button. The action of the tooth 240 on the release button on the annular teeth is in the manner of a ratchet, allowing progressive movement of the first shaft through the bore in the second shaft in one direction but preventing movement in the reverse direction. Preventing unwanted movement of the first shaft 218 relative to the second shaft 220 means that the inward displacement of the cup engaging limbs 210 (so that the inwardly directed fingers 212 engage the lip 256 on the cup component) is locked in, so that the cup component is locked in engagement with the support member 204. The cup component 202 can then be manipulated by means of a handle which is connected to the first shaft by being screwed into threaded bore 226. Impaction forces can be applied to the cup component through the handle.

Once the cup component has been placed and impacted, the handle can be unscrewed from threaded bore 226 and discarded. In order to remove the instrument 200 from the cup component 202 and disassemble the assembly 100, the user again positions his (or her) first and second fingers on opposite sides of the collar 229 of the second shaft, between the peripheral flange 230 and the collar 229, and positioning his thumb on the exposed portion 237 of release button 234. By pressing the release button 234 against the biasing forces exerted by the flexible fingers 242, the tooth 240 on the release button is withdrawn from between the annular teeth 224. The first shaft 218 is then able to slide in the bore in the second shaft 220, in an upward direction (away from the cup component), allowing the jaw members 208 to pivot about the live spring by which they are connected to the circular plate 206 so that the control limbs 214 move inwardly and the cup engaging limbs 210 move outwardly.

In some embodiments, the live spring and/or jaw members are biased toward a disengaged position at which the cup engaging limbs, and in particular inwardly directed fingers 212, are disengaged from the lip 256 of the cup so that the instrument can easily be removed from the cup component. In other embodiments, the live spring and/or jaw members are biased toward a partially engaged position at which the cup engaging limbs, and in particular inwardly directed fingers 212, are partially engage the lip 256 of the cup to prevent the instrument from becoming entirely free and, for example, falling off, but with only a small force, so that the instrument can easily be removed by pulling it from the cup component so that the live spring and/or jaw members flex to release form the lip 256. In other embodiments, the live spring and/or jaw members are not biased toward the partially engaged position nor toward the disengaged position.

The invention claimed is:

1. An instrument for positioning a hollow cup component of an orthopaedic joint prosthesis, comprising:
   a support member having a plurality of jaw members unitarily formed around a periphery of the support member, each of the jaw members having a cup engaging limb which extends from the support member in a first direction to be received in a recess on an external side wall of the cup component, wherein each jaw member is pivotable between an engaged position in which the cup engaging limbs are displaced inwardly and a disengaged position in which the cup engaging limbs are displaced outwardly allowing the cup component to be removed from between the jaw members, and
   an actuator operable to adopt an engaged configuration in which the actuator acts on all the jaw members to urge them into the engaged position or a disengaged configuration in which the actuator does not act on any of the jaw members to urge them into the engaged position and all the jaw members can adopt the disengaged position.

2. The instrument of claim 1, and which includes at least three jaw members unitarily formed around the periphery of the support member.

3. The instrument of claim 2, and which includes at least three groups of jaw members, each group of jaw members including a plurality of jaw members, and each group of jaw members being spaced from adjacent groups of jaw members around a periphery of the support member by a gap including no jaw members.

4. The instrument of claim 1, in which each jaw member is biased towards its disengaged position.

5. The instrument of claim 1, wherein each jaw member is connected to the support member by a live hinge.

6. The instrument of claim 1, in which the actuator comprises a first part comprising a first shaft which can engage the support member and a second part arranged so that it extends parallel to the first shaft and wherein the first part is slidingly received within the second part.

7. The instrument of claim 6, wherein the second shaft has an upper part and a lower part, the lower part being arranged to engage each pivotable support member, and the upper part and lower part defining between them an actuator recess on an outer side of the actuator arranged to receive a pair of digits of a user in use.

8. The instrument of claim 7, wherein the actuator recess includes a first portion and a second portion on opposed sides of the second shaft.

9. The instrument of claim 8, wherein the actuator recess extends entirely around a central longitudinal axis of the actuator.

10. The instrument of claim 1, wherein the actuator includes a releasable lock operable to lock the actuator in the engaged configuration.

11. The instrument of claim 10, wherein the releasable lock is a ratchet mechanism.

12. The instrument of claim 10, wherein the releasable lock includes a button part which stands proud of the actuator and is accessible by a user to release the releasable lock.

13. The instrument of claim 12, in which the actuator comprises a first part comprising a first shaft which can engage the support member and a second part arranged so that it extends parallel to the first shaft and wherein the first part is slidingly received within the second part and wherein the second shaft has an upper part and a lower part, the lower part being arranged to engage each pivotable support member, and the upper part and lower part defining between them an actuator recess on an outer side of the actuator arranged to receive a pair of digits of a user in use and wherein the button is provided in the upper part of the actuator.

14. The instrument of claim, in which each jaw member includes a control limb which is connected to the cup engaging limb at or adjacent to the periphery of the support member, and which has an inner surface which extends inwardly from the edge of the support member where it can be acted on by an outer surface of the actuator.

15. An instrument of claim, wherein the actuator includes an attachment formation by which a handle can be releasably attached to the instrument.

* * * * *